United States Patent
Dumont et al.

(10) Patent No.: US 9,266,132 B2
(45) Date of Patent: Feb. 23, 2016

(54) METHOD AND BOTTLE FOR DISPENSING A FLUID PRODUCT

(75) Inventors: Pierre Dumont, Incheville (FR); Jean-Luc Marcel Octau, Intraville (FR); Emmanuel Mauduit, Rouen (FR)

(73) Assignee: ALBÉA LE TREPORT S.A.S (FR)

( * ) Notice: Subject to any disclaimer, the term of this patent is extended or adjusted under 35 U.S.C. 154(b) by 822 days.

(21) Appl. No.: 13/275,913

(22) Filed: Oct. 18, 2011

(65) Prior Publication Data

US 2012/0090730 A1 Apr. 19, 2012

(30) Foreign Application Priority Data

Oct. 18, 2010 (FR) ...................................... 10 04092

(51) Int. Cl.
*B65B 1/04* (2006.01)
*B05B 11/00* (2006.01)
(Continued)

(52) U.S. Cl.
CPC ............ *B05B 11/0056* (2013.01); *A45D 34/02* (2013.01); *A61M 11/006* (2013.01); *B05B 11/0018* (2013.01); *B05B 11/3047* (2013.01); *B05B 11/3074* (2013.01); *A45D 2200/056* (2013.01); *B05B 11/3026* (2013.01); *B65B 3/14* (2013.01)

(58) Field of Classification Search
CPC ....... F04B 39/12; F04B 39/121; A62C 11/00; B67C 3/28; G01F 11/00; B65B 1/04; B65B 3/04
USPC ........... 141/2, 3, 18, 20, 65, 113, 311 R, 348, 141/349, 350; 222/159, 321.1, 321.2, 222/321.4, 321.7, 321.9, 385; 417/437; 29/888.02; 239/333, 567
See application file for complete search history.

(56) References Cited

U.S. PATENT DOCUMENTS 3,997,086 A * 12/1976 Shay .............................. 222/385
4,804,109 A * 2/1989 Vanderjagt ...................... 222/38
(Continued)

FOREIGN PATENT DOCUMENTS

CH 258147 A 11/1948
DE 1087513 B 9/1960
(Continued)

OTHER PUBLICATIONS

French Search Report; Application No. FR 1004092; Issued: Jun. 8, 2011; 6 pages.

*Primary Examiner* — Jason K Niesz
*Assistant Examiner* — Andrew Schmid
(74) *Attorney, Agent, or Firm* — St Onge Steward Johston and Reens LLC

(57) ABSTRACT

A method of dispensing a fluid product by using a dispensing bottle which includes a rigid body in which a reservoir for packaging the fluid product is formed and a device for taking off the packaged fluid product that is mounted sealingly on the body, the body also being equipped with a valve for filling the reservoir, the method, prior to the initial filling of the reservoir with fluid product, making provision for putting the empty reservoir in communication with an air suction device and activating the device in order to create a negative pressure inside the reservoir; subsequently effecting the initial filling of the reservoir by putting a product source in sealed communication with the reservoir by means of the valve; dispensing the packaged fluid product by actuating the take-off device.

18 Claims, 7 Drawing Sheets

(51) Int. Cl.
*A45D 34/02* (2006.01)
*A61M 11/00* (2006.01)
*B65B 3/14* (2006.01)

(56) References Cited

U.S. PATENT DOCUMENTS

| | | | | |
|---|---|---|---|---|
| 5,692,650 | A * | 12/1997 | Wolter et al. | 222/321.9 |
| 5,791,527 | A * | 8/1998 | Giuffredi | 222/321.9 |
| 6,354,469 | B1 * | 3/2002 | Pozzi | 222/189.09 |
| 6,415,959 | B1 * | 7/2002 | Bougamont et al. | 222/159 |
| 6,863,093 | B2 * | 3/2005 | Garcia et al. | 141/2 |
| 7,222,646 | B2 * | 5/2007 | Gupta | 141/2 |
| 7,665,635 | B2 * | 2/2010 | Ramet | B05B 11/0056 141/113 |
| 8,695,896 | B2 * | 4/2014 | Tu | 239/333 |
| 2001/0013379 | A1 * | 8/2001 | Yquel | 141/20 |
| 2002/0179635 | A1 * | 12/2002 | Incardona et al. | 222/92 |
| 2003/0150876 | A1 * | 8/2003 | Walters et al. | 222/153.13 |
| 2005/0006412 | A1 * | 1/2005 | Albisetti et al. | 222/321.9 |
| 2009/0261127 | A1 * | 10/2009 | Pan | 222/256 |
| 2010/0025432 | A9 * | 2/2010 | Yapaola et al. | 222/175 |
| 2010/0089945 | A1 * | 4/2010 | Law et al. | 222/1 |
| 2010/0199606 | A1 * | 8/2010 | Behar et al. | 53/432 |
| 2012/0090730 | A1 * | 4/2012 | Dumont et al. | 141/2 |
| 2012/0255647 | A1 * | 10/2012 | Dumont et al. | 141/311 R |
| 2012/0312842 | A1 * | 12/2012 | Dumont et al. | 222/321.9 |
| 2012/0312843 | A1 * | 12/2012 | Dumont et al. | 222/321.9 |
| 2013/0019991 | A1 * | 1/2013 | Muller | 141/18 |
| 2013/0068796 | A1 * | 3/2013 | Hui | G01F 11/028 222/256 |
| 2013/0126639 | A1 * | 5/2013 | Tu | 239/302 |
| 2013/0320036 | A1 * | 12/2013 | Muller et al. | 222/51 |
| 2014/0027474 | A1 * | 1/2014 | Dumont et al. | 222/321.1 |
| 2014/0060695 | A1 * | 3/2014 | Dumont et al. | 141/18 |
| 2014/0069551 | A1 * | 3/2014 | Lasnier et al. | 141/18 |
| 2014/0086770 | A1 * | 3/2014 | Octau et al. | 417/437 |
| 2014/0102584 | A1 * | 4/2014 | Lasnier et al. | 141/18 |
| 2014/0137983 | A1 * | 5/2014 | Tu | 141/113 |

FOREIGN PATENT DOCUMENTS

| | | | | |
|---|---|---|---|---|
| DE | 2651869 | A1 | 5/1978 | |
| FR | 2854131 | A1 * | 10/2004 | B65B 3/14 |
| GB | 2229380 | A * | 9/1990 | B05B 11/00 |
| JP | 2013107708 | A * | 6/2013 | |

* cited by examiner

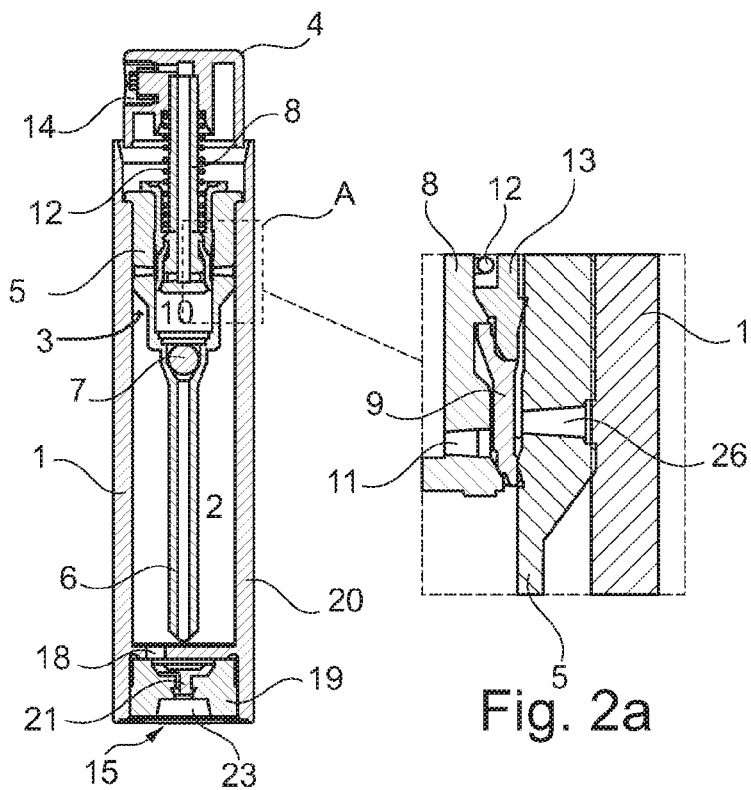
Fig. 2
Fig. 2a
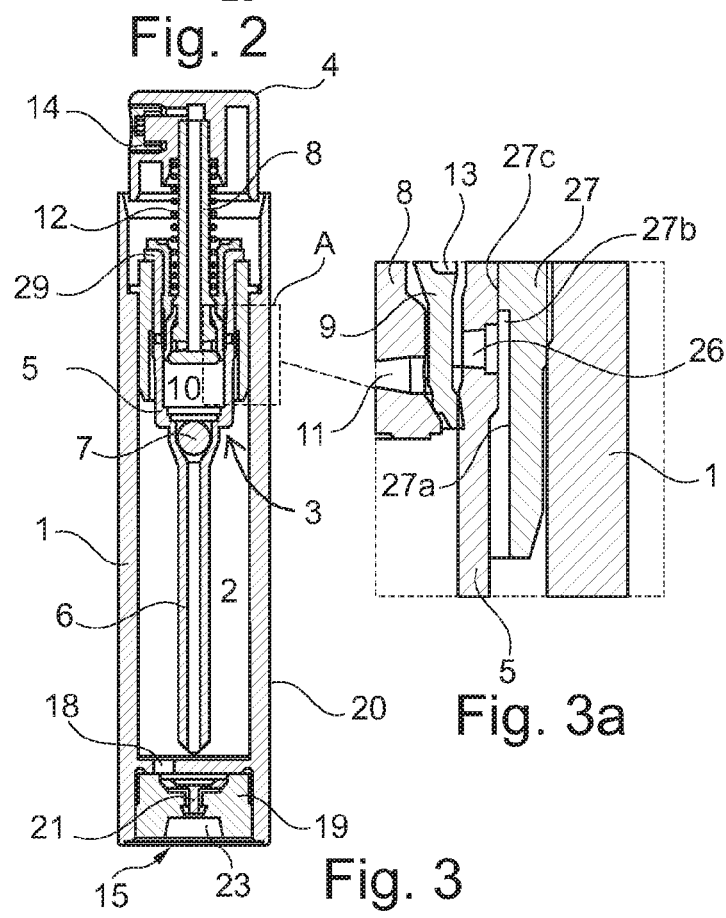
Fig. 3
Fig. 3a

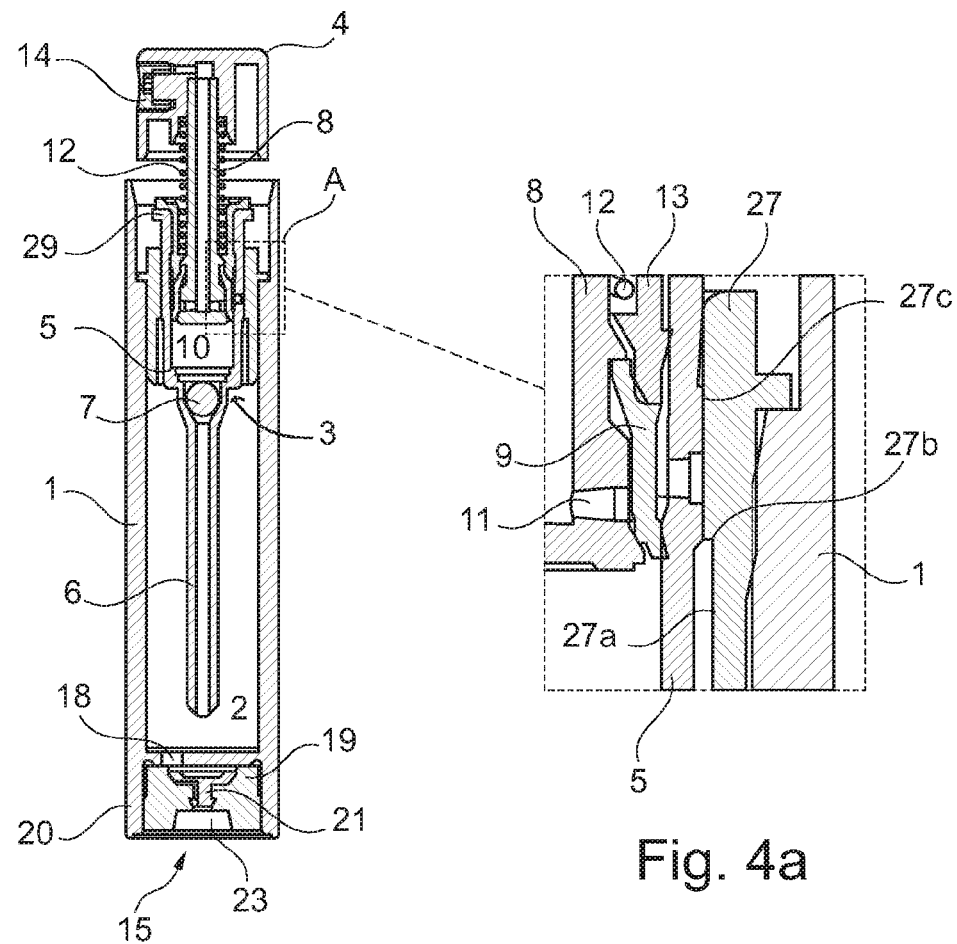
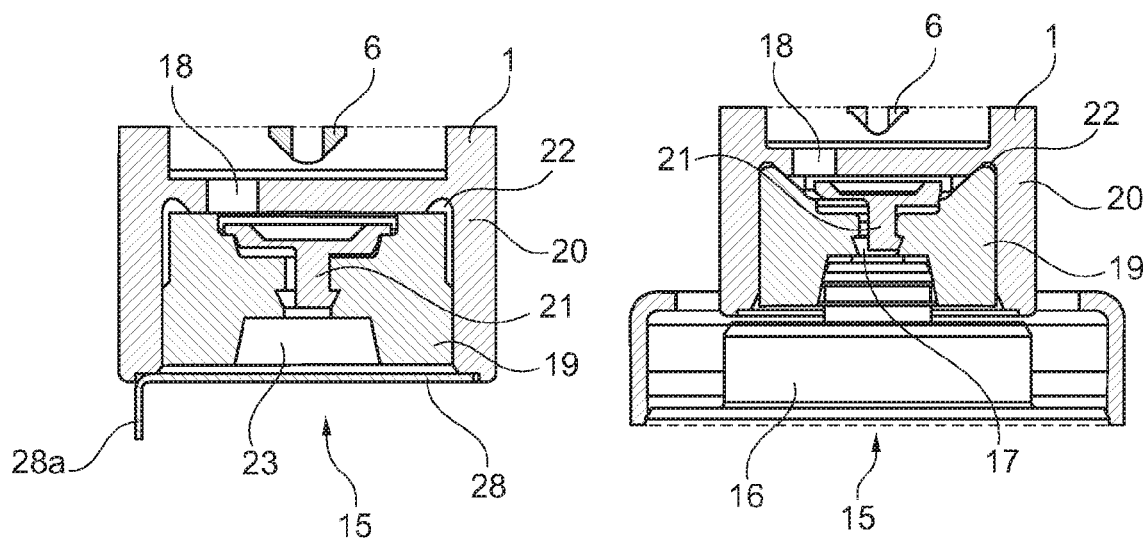

METHOD AND BOTTLE FOR DISPENSING A FLUID PRODUCT

CROSS-REFERENCE TO RELATED APPLICATIONS

The present application claims priority of French patent application No. 10 04092 filed on Oct. 18, 2010, the content of which is incorporated herein by reference.

FIELD OF THE INVENTION

The invention concerns a method of dispensing a fluid product by means of a dispensing bottle as well as a bottle for dispensing such a product. In particular, the product may be liquid, for example care cosmetic, make-up or perfume, or pharmaceutical.

BACKGROUND OF THE INVENTION

The dispensing bottle comprises a rigid body in which a reservoir for packaging the product is formed, as well as a device for taking off the packaged product that is mounted sealingly on said body. In particular, the take-off device may comprise a manual-actuation pump that is supplied with packaged product, said pump being arranged to dispense the product under pressure, for example in the form of an aerosol.

In an example application, the bottles according to the invention enable samples of product to be dispensed, in particular for a volume of product packaged in the reservoir that is between 1 and 10 ml. In particular, the samples thus dispensed can enable a client to test the product, the bottles then being referred to as sample test bottles. In a variant, the bottles may be so-called "handbag" bottles in that they make it possible to easily transport a small volume of product, in contradistinction to bottles with a larger capacity, which are in general heavy and bulky since they are expensive.

In these applications, for example for logistic reasons, reasons of practicality or for environmental recycling reasons, it may be desirable to be able to recharge the reservoir with product from a source of said product. This is because it is not very practical for a user to fill the reservoir by means of a small funnel and not ecological to throw away an empty bottle in order to replace it with a full one constituting a refill.

Dispensing bottles are already offered for sale in which the body is equipped with a reservoir filling valve that is arranged to enable a product source to be put in communication with said reservoir. In particular, the valve can open by pressing on the nozzle of the pump of a source bottle, which it is necessary to actuate repeatedly in order to effect the filling, which is an action that is not very intuitive for the user.

There is also known, in particular from the document FR-2 854 131, a method of filling a reservoir that provides for the prior emptying of the reservoir by means of an airless dispensing pump in order to create a negative pressure inside said reservoir, then putting a product source in communication with said pump in order to effect filling by suction through said pump. However, this design requires the use of a dedicated pump that allows both filling and dispensing.

In addition, this design does not allow initial filling of the dispensing bottle in a satisfactory fashion, whether by the users and/or by the distributors at the point of sale. This is because, in particular when the bottle is assembled in the packaging factory, an initial filling of the reservoir with product must be carried out prior to the recharging by suction. Thus the distributors of these bottles must have a dedicated bottle for each of the products that it offers for sale.

In particular, for dispensing product samples, a sample test bottle must be provided for each of the products since filling said bottle cannot be carried out simply at the time of handing to the customer. Thus product distributors have a considerable number of sample test bottles that all resemble each other and among which they must find the one that they seek to hand to a customer.

Moreover, some makes may require that the bottles for their product not be fillable subsequently by the users, while benefitting from a simplification in the initial filling of said bottle. In particular, it may be required for the sample test bottles to be fillable only once.

SUMMARY OF THE INVENTION

The invention aims to improve the prior art by proposing in particular a method and dispensing bottle the initial filling of which with product can be carried out in a particularly simple and versatile fashion, in particular at the distributors, without any obligation to be able to fill said bottle subsequently or to use a specific sampling device.

To this end, and according to a first aspect, the invention proposes a method of dispensing a fluid product by means of a dispensing bottle comprising a rigid body in which a reservoir for packaging said product is formed, said bottle also comprising a device for taking off the packaged product that is mounted sealingly on said body, said body also being equipped with a valve for filling said reservoir that is arranged to enable a product source to be put in communication with said reservoir, said method making provision for:
  prior to the initial filling of the reservoir with product, putting said empty reservoir in communication with an air suction device and activating said device in order to create a negative pressure inside said reservoir;
  subsequently performing the initial filling of the reservoir by putting a product source in sealed communication with the reservoir by means of the valve so that the negative pressure causes filling of said reservoir by suction of the product contained in said source;
  dispensing the packaged product by actuating the take-off device.

According to a second aspect, the invention proposes a bottle for dispensing a fluid product comprising a rigid body in which a reservoir intended for packaging said product is formed, said bottle also comprising a device for taking off the packaged product that is mounted sealingly on said body, said body also being equipped with a valve for filling said reservoir that is arranged to enable a product source to be put in communication with said reservoir, the reservoir being empty of product and having a negative air pressure that is arranged to be able to subsequently effect the initial filling of the reservoir with product by putting a product source in sealed communication with said reservoir by means of the valve so that said negative pressure causes the filling of said reservoir by suction of the product contained in said source.

BRIEF DESCRIPTION OF THE DRAWINGS

Other objects and advantages of the invention will emerge from the following description given with reference to the accompanying figures, in which:

FIG. 2 is a view in longitudinal section of a dispensing bottle according to one embodiment of the invention, FIG. 2a being an enlarged view of zone A in FIG. 2;

FIG. 3 is a view in longitudinal section of a dispensing bottle according to one embodiment of the invention, FIG. 3a being an enlarged view of zone A in FIG. 3;

FIG. 4 is a view in longitudinal section of a dispensing bottle according to one embodiment of the invention in which the take-off device is in the storage position, FIG. 4a being an enlarged view of zone A in FIG. 4;

FIGS. 5a-5b show in longitudinal section the bottom end of a dispensing bottle that is equipped with a filling valve, said valve being respectively in the stable sealed closure state (FIG. 5a) and in the stressed state of putting in sealed communication with a take-off tube of a product source (FIG. 5b)

DETAILED DESCRIPTION OF THE INVENTION

Figure 1:
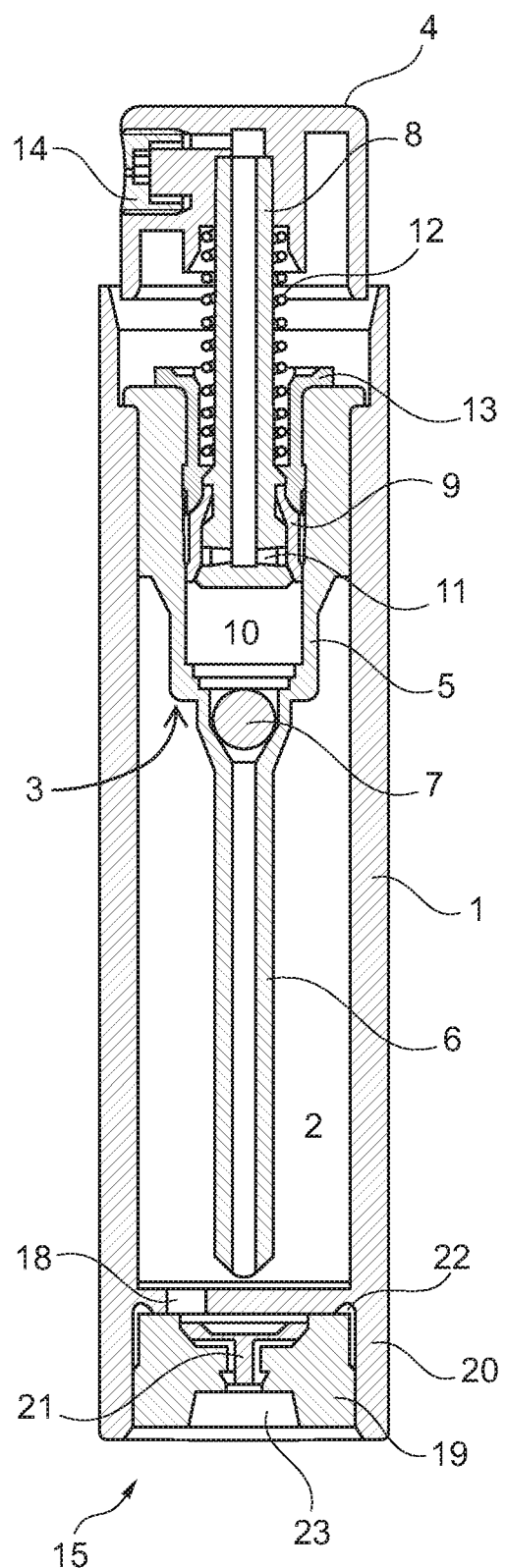
FIG. 1 is a view in longitudinal section of a dispensing bottle according to one embodiment of the invention.

In the description, the terms in relation to positioning in space are taken with reference to the position of the bottle shown in FIG. 1.

In relation to the figures, a description is given below of a bottle intended to contain a fluid product with a view to dispensing thereof, as well as a dispensing method using such a bottle. In particular examples, the product may be a liquid, in particular a care cosmetic, make-up or perfume product, or a pharmaceutical product.

The bottle comprises a rigid body 1 in which a reservoir 2 for packaging the product is formed. In particular, the body 1 has sufficient rigidity so that the volume of the reservoir 2 remains substantially constant. In a particular application, the reservoir 2 may have a capacity of between 1 and 10 ml so as to enable product samples to be dispensed. In relation to FIG. 6, the body 1 is intended to be inserted in a cladding (not shown).

The body 1 may be in a single piece, for example produced by injection blowing or extrusion blowing, or in several parts injected and then assembled, for example by ultrasonic welding, made from rigid plastics material, metal, for example aluminium, or glass.

The bottle also comprises a device for taking off the packaged product that is mounted sealingly on the body 1, in particular in the top opening of said body. In the embodiments shown, the take-off device comprises a dispensing pump 3 actuated manually by means of a push button 4 that is supplied with the pressurised product with a view to dispensing thereof.

The pump 3 comprises a body 5 equipped with means of supplying a packaged product. In the figures, the supply means comprise a plunger tube 6 disposed in the reservoir 2, said tube being equipped with a valve 7 for admitting the product into the pump 3. The push button 4 is mounted on the nozzle 8 of the pump 3, which comprises a piston 9 mounted around said nozzle in order to delimit a metering chamber 10 in the body 1. The piston 9 enables the supply orifices 11 of the nozzle 8 to open—or respectively close—over a dispensing—or respectively suction—travel of said nozzle.

The push button 4 comprises an upper region enabling the user to exert finger pressure on said push button in order to be able to move it axially over its travel for actuation of the pump 3, the return of the push button 4 over its suction travel being conventionally effected by a spring 12. In the embodiment shown, the interior of the body 5 of the pump 3 is equipped with an extender 13 on which the bottom end of the spring 12 is in abutment.

The push button 4 is equipped with a spray head 14 that is arranged to distribute an aerosol of the product radially. However, the invention is not limited to a particular method of dispensing the product. In particular, for a nasal spray piece, the push button 4 may afford axial dispensing of the product and another type of take-off device may be envisaged.

The body 1 of the bottle is equipped with a valve 15 for filling the reservoir 2 that is arranged to put a product source 16 in communication with said reservoir. The product source 16 may comprise a source reservoir on which a take-off tube 17 is disposed, the filling of the reservoir 2 with product being achieved by mounting said tube in sealed abutment on the valve 15, which is arranged to open reversibly.

In particular, it is possible to use, as a product source 16, a spare bottle with a greater capacity (FIG. 6), said bottle being equipped with a pump the push button of which is removed to enable the nozzle to be arranged in sealed abutment on the valve 15. This is because, apart from the opening of the valve 15, the sealed abutment causes the opening of the pump in order to enable the filling product to pass through it.

According to another embodiment, the source reservoir is formed inside a flexible pouch that can be filled with product without air or gas in order to preserve said product properly. Transfer of the product into the reservoir 2 is then possible in all positions and the flexible pouch cannot be diverted from its role of source since it is without a propellant gas or internal pressure, or a push button for actuating any pump associated with the take-off tube 17.

In the embodiments shown, the filling valve 15 is disposed on the bottom end of the body 1 so as in particular to fill the reservoir 2 through the bottom of the bottle, which is an intuitive action.

To do this, the bottom end of the body 1 has an orifice 18 for communication with the reservoir 2 and the valve 15 has a seat 19 that is movable and/or deformable between a stable state of sealed closure of the orifice 18 of the reservoir 2 and a stressed state of opening of said orifice for putting the product source 16 in sealed communication with said reservoir.

In relation to FIGS. 1 to 5, the body 1 has a bottom trim 20 in which a rigid shutter 21 is formed, said trim having a bottom in which the orifice 18 is formed, said bottom having a peripheral groove 22. The valve 15 also comprises a deformable seat 19, for example produced from elastomeric material, which has a bottom housing 23 for entry of the take-off tube 17, said seat in the stable closure state being in sealed abutment on the shutter 21 (FIG. 5a). The abutment of the take-off tube 17 in the seat 19 causes the reversible creep of said seat in the groove 22 (FIG. 5b) so as to release the sealed abutment and therefore break the seal between said seat and the shutter 21 in order to put the housing 23 in communication with the orifice 18.

Figure 6A:
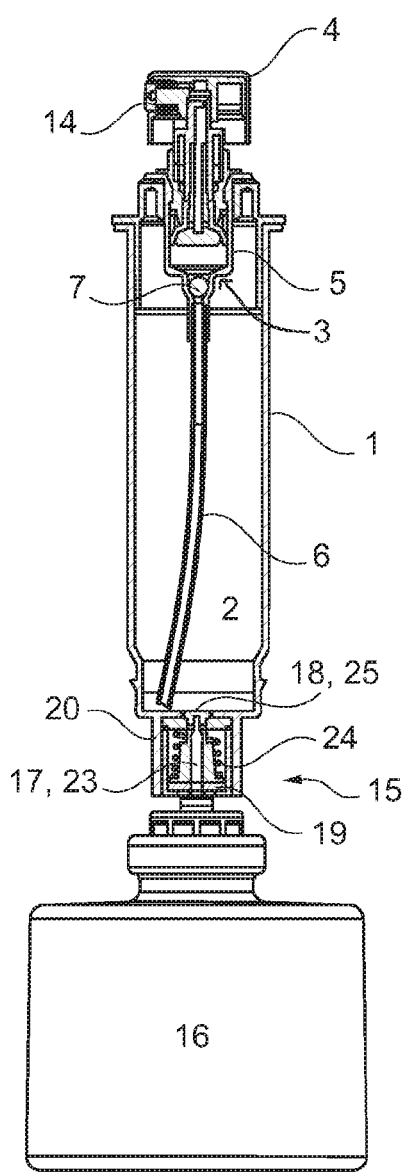
FIGS. 6a-6b are views in longitudinal section of a dispensing bottle according to one embodiment of the invention, the filling valve being mounted on the nozzle of the pump of a product source bottle, respectively before filling in the stable sealed closure state (FIG. 6a) and during filling in the stressed putting in communication state (FIG. 6b).
Figure 6B:
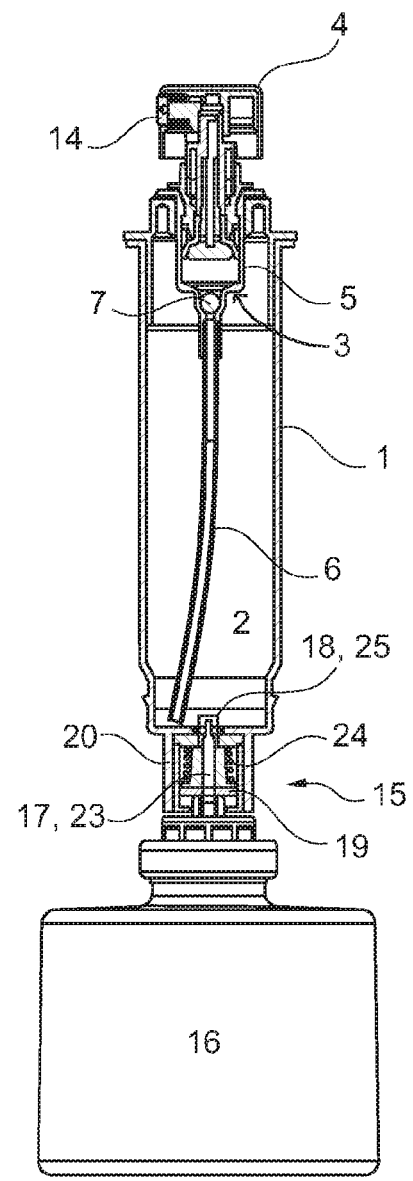

In relation to FIG. 6, the valve 15 comprises a movable seat 19 provided with a bottom housing 23 for entry of the take-off tube 17, said seat being mounted in reversible translation in the trim 20 by means of a return spring 24. The seat 19 has an end piece 25 that is mounted in the orifice 18, said end piece being provided with passages that are respectively closed in the stable position and open in the pressed-in position in order to put the housing 23 in communication with said orifice.

The dispensing method makes provision, prior to the initial filling of the reservoir 2 with product, for putting said empty product reservoir in communication with an air suction device and activating said device in order to create a negative pressure inside said reservoir.

Figure 7A:
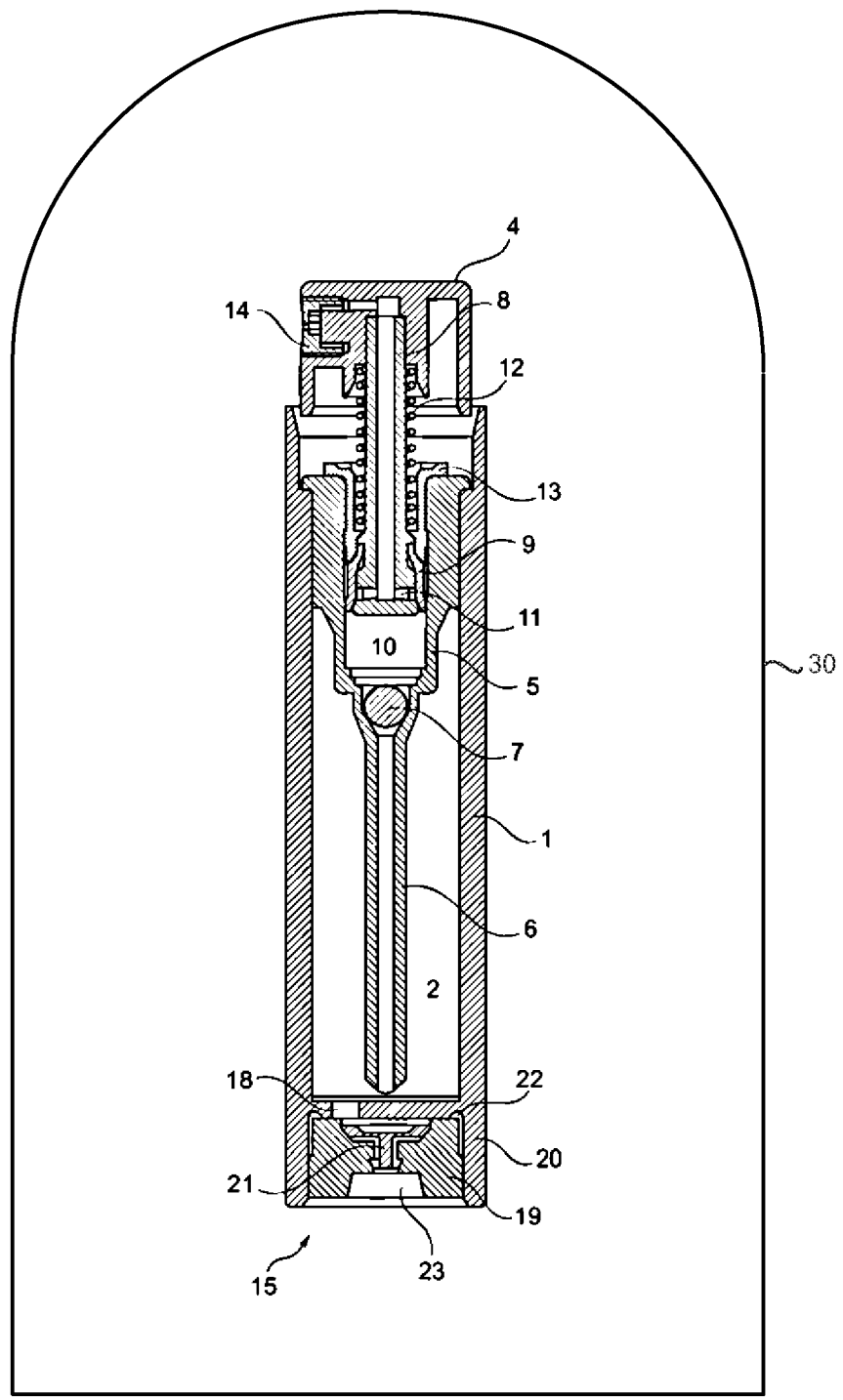
FIGS. 7a-7c are views in longitudinal section of a dispensing bottle according to the invention showing the air suction device.

According to one embodiment, shown in FIG. 7a, the air suction device comprises a vacuum bell 30 in which the dispensing bottle is disposed, the sealed mounting of the take-off device (e.g., pump 3) on the body 1 being achieved after activation of said bell. Thus the negative pressure is formed in the reservoir 2 and then the take-off device (e.g., pump 3) is mounted sealingly so as to maintain said negative pressure.

Figure 7B:
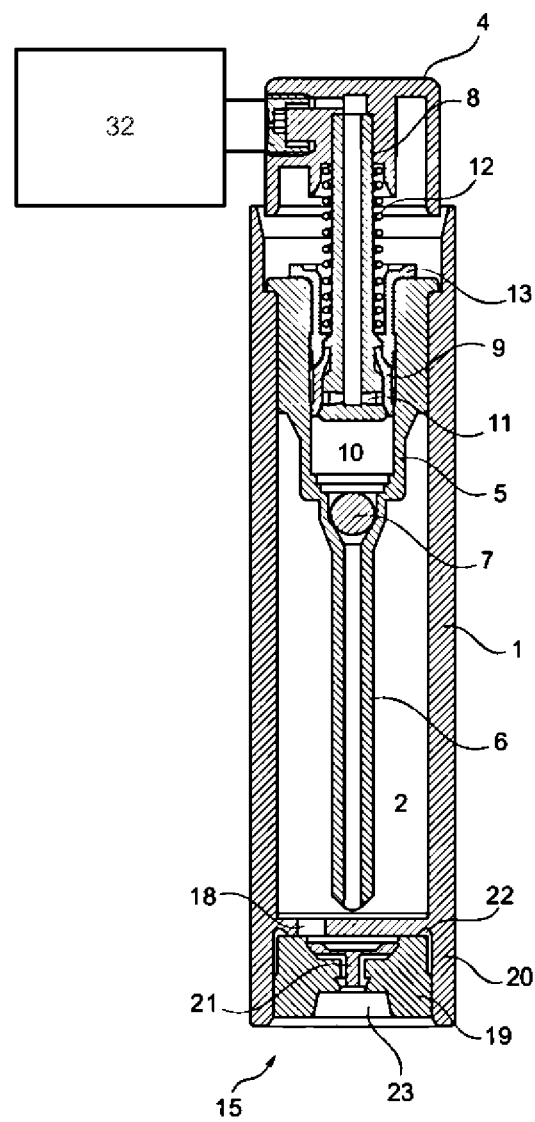
Figure 7C:
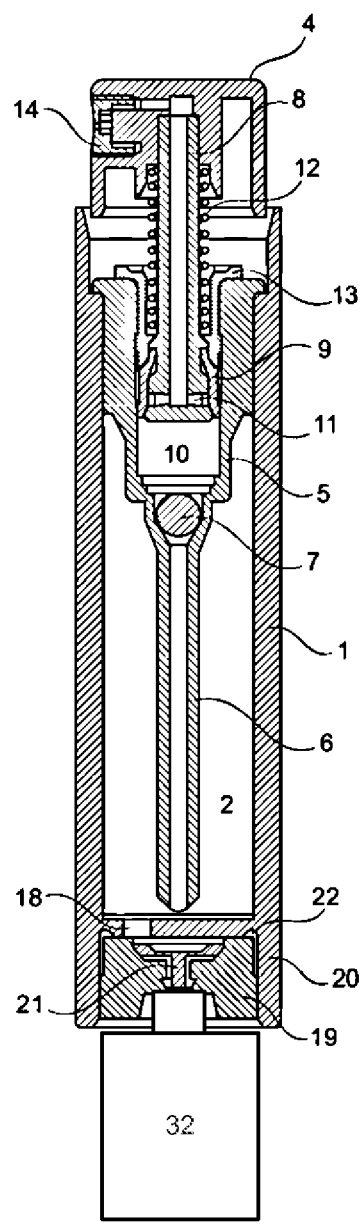

According to another embodiment, shown in FIG. 7b, the air suction device, for example a vacuum pump 32, is put in communication with the take-off device (e.g., pump 3) after sealed mounting thereof on the body 1, the suction of the air from the reservoir 2 being effected through said take-off device. In a variant, shown in FIG. 7c, the suction of air could be effected through the valve 15 by making provision to put it into communication with the air suction device, e.g., vacuum pump 32, after sealed mounting of the take-off device (e.g., pump 3) on the body 1.

The dispensing method makes provision for subsequently effecting the initial filling of the reservoir 2 by putting a product source 16 in sealed communication with said reservoir by means of the valve 15 so that the negative pressure causes the filling of said reservoir by suction of the product contained in said source. Next, the customer can actuate the take-off device (e.g., pump 3) in order to dispense the packaged product.

This is because, after arrangement of the take-off tube 17 in the housing 23, a single press causes the opening of the valve 15, as well as possibly the opening of the pump of the source bottle 16, so as to form a transfer path of product between the source 16 and the reservoir 2. Compensation for the negative pressure then allows filling. Next, when the reservoir 2 is filled, the suction negative pressure becomes zero and the valve 15 is then closed when the take-off tube 17 is withdrawn and the product contained in the reservoir 2 can be dispensed subsequently by means of the take-off device (e.g., pump 3).

The dispensing bottle that is supplied to the distributors is therefore empty of product and has a negative air pressure, said negative pressure making it possible to subsequently effect the initial filling, in particular at the time of handing the bottle to the customer according to the product that they wish to purchase and/or test. The method therefore allows a particularly versatile initial filling, which in particular allows simplified management of the bottles by the distributors, in particular sample test bottles.

The versatility of the dispensing method can also be improved by providing the association of a label on the body 1 at the time of initial filling of the reservoir 2 with product, in particular according to said product. The label can have a detachable part comprising a sales offer particular to the distributor in order to encourage the customer to return and purchase the sampled product.

In relation to FIGS. 1 and 2, the take-off device (e.g., pump 3), is of the airless type without the take up of air in the reservoir 2 in compensation for the volume of product dispensed. To do this, the body 5 of the pump 3 of FIG. 1 has no vent hole.

However, since pumps 3 with vent hole 26 are the most usual, it may be advantageous to create a negative pressure in the reservoir 2 even with this type of pump. To do this, FIG. 2 has a body 5 provided with a vent hole 26 that is closed off sealingly by mounting thereof in the rigid body 1 (FIG. 2a). In particular, the seal between the body 5 and rigid body 1 is then made at least below the vent hole 26 so as to prevent the passage of air from the pump 3 into the reservoir 2 by means of said hole. In FIG. 2, the seal is also achieved above the vent hole 26, which does not impair the functioning without take up of air and is a little simpler to achieve.

The product sample without take up of air in the reservoir 2 makes it possible to create in said reservoir a negative pressure that increases along with dispensing. In particular, in order to ensure total emptying of the reservoir 2, the ceiling of air above the product during initial filling must be such that the negative pressure reached at the end of emptying is at a maximum equal to the negative pressure achievable by the pump 3.

In this embodiment, the dispensing method then provides for the possibility of subsequent filling of the reservoir 2 by the sealed putting in communication of the product source 16 with said reservoir by means of the valve 15 so that the negative pressure causes the filling of said reservoir by suction of the product contained in said source.

In relation to FIGS. 3 and 4, the product is taken off with take up of air in the reservoir 2 so as to prevent the subsequent filling of said reservoir by suction. To do this, the pump 3 comprises a vent hole 26 that is arranged to make it possible to compensate for the volume of product taken off in the reservoir 2 with air.

In relation to FIG. 3, the pump 3 is mounted in the body 1 by means of a sleeve 27 in which the body 5 is fitted sealingly. The vent hole 26 is formed in the body 2 radially opposite an increased diameter 27a that is formed on the sleeve 27 so as to leave free said hole in order to enable air to be taken into the reservoir 2 (FIG. 3a).

According to one embodiment, the dispensing method may, prior to the initial filling of the reservoir 2 with product, provide for the mounting of the take-off device (e.g., pump 3) on the body 1 in a storage position in which the airtightness of the reservoir 2 is reinforced, said take-off device subsequently being moved into a dispensing position. This is because, in the dispensing position, the static airtightness of the reservoir 2 having a negative pressure may be insufficient, in particular in the presence of a vent hole 26, to guarantee the maintenance of this negative pressure at the end of prolonged storage.

In addition, still in order to improve the maintenance of the negative pressure over time, the filling valve 15 may be reversibly covered with a sealing cap 28. In relation to FIG. 5a, the cap 28 is welded in a recess formed on the free end of the trim 20 so that said cap completely covers the valve 15, said cap having a free edge 28a enabling it to be withdrawn with a view to the initial filling.

In relation to FIGS. 3 and 4, the pump 3 is mounted so as to be able to slide with respect to the body 1 between an upper storage position in which the vent hole 26 is closed off (FIG. 4) and a lower dispensing position (FIG. 3) in which said vent hole is free to enable air to be taken in.

In particular, the body 5 is mounted in the sleeve 27 with clamping suitable for enabling sliding, the passage between these positions being achieved by pressing on the push button 4 when the pump 3 is first actuated. The sleeve 27 has a step 27b delimiting an upper diameter 27c for sealed mounting of the body 5 in order to close off the vent hole 26 and an increased lower diameter 27a leaving said vent hole free, said pump body having a stop 29 for the end of sliding travel in the sleeve 27.

What is claimed is:

1. A method for the dispensing of a fluid product by means of a dispensing bottle comprising a rigid body in which a reservoir for packaging said product is formed, said bottle also comprising a take-off device for taking off the packaged product that is mounted sealingly on said body, said body also being equipped with a valve, separate from the take-off device, for filling said reservoir that is arranged to enable a source of product to be put in communication with said reservoir, said method comprising the steps of:

prior to the initial filling of the reservoir with product, putting said empty reservoir in communication with an air suction device and activating said air suction device in order to create a negative pressure inside said reservoir, said air suction device being different from the take-off device for taking off the packaged product;

subsequently performing the initial filling of the reservoir by putting a source of product in sealed communication with the reservoir by means of the valve so that the negative pressure causes filling of said reservoir by suction of the product contained in said source; and dispensing the packaged product by actuating the take-off device.

2. The dispensing method according to claim 1, characterised in that the air suction device comprises a vacuum bell in which the dispensing bottle is disposed, the sealed mounting of the take-off device on the body being effected after activation of said vacuum bell.

3. The dispensing method according to claim 1, characterised in that the air suction device is put in communication with the take-off device after sealed mounting thereof on the body, the suction of the air from the reservoir being effected through said take-off device.

4. The dispensing method according to claim 1, characterised in that the air suction device is put in communication with the valve after sealed mounting of the take-off device on the body, the suction of air from the reservoir being effected through said valve.

5. The dispensing method according to claim 1, characterised in that the product source comprises a source reservoir on which a take-off tube is disposed, the filling of the packaging reservoir being effected by mounting said tube in sealed abutment on the valve, which is arranged so as to open reversibly in order to suck product from said source reservoir into said packaging reservoir.

6. The dispensing method according to claim 1, characterised in that, prior to the initial filling of the reservoir with product, it provides for the mounting of the take-off device on the body in a storage position in which the airtightness of said reservoir is reinforced, said take-off device being moved subsequently into a dispensing position.

7. The dispensing method according to claim 6, characterised in that the take-off device is mounted so as to slide with respect to the body between an upper storage position and a lower dispensing position, the passage between these positions being effected when the take-off device is first actuated.

8. The dispensing method according to claim 6, characterised in that the take-off device comprises a vent hole that is arranged so as to make it possible to compensate for the volume of product taken off in the reservoir by means of air, said vent hole being closed off in the storage position and free in the dispensing position in order to enable air to be taken up.

9. The dispensing method according to claim 1, characterised in that the product is taken off without the taking up of air in the packaging reservoir so as to create a negative pressure in said reservoir that increases along with dispensing, said method also providing for the subsequent filling of said reservoir by the putting the source product in sealed communication with said reservoir by means of the valve so that the negative pressure causes filling of said reservoir by suction of the product contained in said source.

10. The dispensing method according to claim 1, characterised in that the product is taken off with the taking up of air in the packaging reservoir so as to prevent the subsequent filling of said reservoir by suction.

11. The dispensing method according to claim 1, characterised in that it provides for the association of a label on the body at the time of initial filling.

12. A bottle for dispensing a fluid product comprising a rigid body in which a reservoir intended for packaging said product is formed, said bottle also comprising a take-off device for taking off said packaged product that is mounted sealingly on said body, said body also being equipped with a valve, separate from the take-off device, for filling said reservoir that is arranged to enable a product source to be put in communication with said reservoir, said bottle being characterised in that the reservoir is empty of product and has a negative air pressure, due to the reservoir being put in communication with an air suction device, said air suction device being different from the take-off device for taking off the packaged product, that is arranged to be able to subsequently effect the initial filling of the reservoir with product by putting a product source in sealed communication with said reservoir by means of the valve so that said negative pressure causes the filling of said reservoir by suction of the product contained in said source.

13. The dispensing bottle according to claim 12, characterised in that the take-off device is of the type without take up of air in the packaging reservoir in compensation for the volume of product dispensed.

14. The dispensing bottle according to claim 12, characterised in that the take-off device comprises a vent hole that is arranged to compensate for the volume of product taken off in the reservoir with air.

15. The dispensing bottle according to claim 14, characterised in that the take-off device is mounted on the body in a storage position in which the vent hole is closed off, said take-off device being movable with respect to the body in a dispensing position which said vent hole is free to enable air to be taken up.

16. The dispensing bottle according to claim 12, characterised in that the filling valve is covered reversibly by a sealing cap.

17. The dispensing bottle according to claim 12, characterised in that the valve has a seat that is movable and/or deformable between a stable state of sealed closure of the packaging reservoir and a stressed state of putting the product source in communication with said reservoir.

18. The dispensing bottle according to claim 12, characterised in that the filling valve is disposed on the lower end of the body.

* * * * *